United States Patent [19]

Maeyama

[11] Patent Number: 5,640,965
[45] Date of Patent: Jun. 24, 1997

[54] PULSIMETER CAPABLE OF PROPERLY EVALUATING AMOUNT OF EXERCISE AT ARBITRARY TIME

[75] Inventor: Hachiro Maeyama, Nara, Japan

[73] Assignee: Cateye Co., Ltd., Osaka, Japan

[21] Appl. No.: 340,608

[22] Filed: Nov. 16, 1994

Related U.S. Application Data

[63] Continuation of Ser. No. 25,168, Mar. 2, 1993, abandoned.

[30] Foreign Application Priority Data

Mar. 6, 1992 [JP] Japan ................................. 4-11424

[51] Int. Cl.$^6$ ............................................. A61B 5/02
[52] U.S. Cl. ........................... 128/687; 128/688; 128/689; 128/690
[58] Field of Search ............................. 128/687–690

[56] References Cited

U.S. PATENT DOCUMENTS

| | | | |
|---|---|---|---|
| 4,086,916 | 5/1978 | Freeman et al. | 128/690 X |
| 4,159,416 | 6/1979 | Brojnik et al. | 128/690 X |
| 4,202,350 | 5/1980 | Walton | 128/690 |
| 4,224,948 | 9/1980 | Cramer et al. | 128/690 |
| 4,807,639 | 2/1989 | Shimizu et al. | 128/690 |

*Primary Examiner*—Angela D. Sykes
*Assistant Examiner*—Stephen Huang
*Attorney, Agent, or Firm*—Banner & Witcoff, Ltd.

[57] ABSTRACT

Pulses detected by an earlobe sensor are inputted in a microcomputer, so that the number of pulses is stored every lapse of a prescribed time. The as-stored numbers of the pulses are so cumulated that an average pulse rate is calculated from the cumulative result. On the other hand, a pulse rate is calculated from the as-stored numbers of pulses, to calculate a consumed calorie. A display part indicates the cumulative result of the pulse rates, the consumed calorie and the like with a lapse time.

12 Claims, 12 Drawing Sheets

FIG. 4

| PULSE RATE | CONSUMED CALORIE PER 2 SEC. | CONSUMED CALORIE PER 1 MIN. |
|---|---|---|
| NOT MORE THAN 70 bpm | 0.033 kcal | 0.99 kcal |
| 71 bpm | 0.033 | 0.99 |
| 72 | 0.033 | 0.99 |
| 73 | 0.034 | 1.02 |
| 74 | 0.035 | 1.05 |
| 75 | 0.036 | 1.08 |
| 76 | 0.038 | 1.14 |
| 77 | 0.040 | 1.20 |
| 78 | 0.042 | 1.26 |
| 79 | 0.044 | 1.32 |
| 80 | 0.046 | 1.40 |
| 81 | 0.049 | 1.47 |
| 82 | 0.053 | 1.59 |
| 83 | 0.056 | 1.68 |
| 84 | 0.060 | 1.80 |
| 85 | 0.063 | 1.89 |
| 86 | 0.066 | 1.98 |
| 87 | 0.070 | 2.10 |
| 88 | 0.073 | 2.19 |
| 89 | 0.077 | 2.31 |
| 90 | 0.080 | 2.40 |
| 91 | 0.085 | 2.55 |
| 92 | 0.091 | 2.73 |
| 93 | 0.096 | 2.88 |
| 94 | 0.101 | 3.03 |
| 95 | 0.106 | 3.18 |
| 96 | 0.112 | 3.36 |
| 97 | 0.117 | 3.51 |
| 98 | 0.122 | 3.66 |
| 99 | 0.127 | 3.81 |

| PULSE RATE | CONSUMED CALORIE PER 2 SEC. | CONSUMED CALORIE PER 1 MIN. |
|---|---|---|
| 100 bpm | 0.1334 kcal | 4.00 kcal |
| 120 | 0.1834 | 5.50 |
| 140 | 0.2334 | 7.00 |
| 160 | 0.2834 | 8.50 |
| 180 | 0.3334 | 10.00 |

1

PULSIMETER CAPABLE OF PROPERLY EVALUATING AMOUNT OF EXERCISE AT ARBITRARY TIME

RELATED APPLICATION

This application is a continuation of application Ser. No. 08/025,168 filed Mar. 2, 1993 now abandoned.

BACKGROUND OF THE INVENTION

1. Field of the Invention

The present invention relates to a pulsimeter, and more particularly, it relates to a pulsimeter which is employed for managing exercise such as jogging.

2. Description of the Background Art

In a conventional pulsimeter, upper and lower limit values of a pulse rate to be counted are so set that warning is given to the user by an alarm when the pulse rate is in excess or below the upper or lower limit value, thereby maintaining the strength of the exercise at a proper level.

Another conventional pulsimeter is adapted to store pulse rate data during exercise. Namely, this pulsimeter stores a pulse rate which is detected every constant period of 5 seconds, 15 seconds or 1 minute, and displays data showing relations between such pulse rates and times after completion of the exercise.

Another conventional pulsimeter cumulates respective times of those elapsing with pulse rates exceeding an upper limit value, between upper and lower limits and below the lower limit, to display the respective cumulated times after completion of the exercise.

In such a conventional pulsimeter, however, it is impossible to grasp the amount of exercise in real time, although the logged pulse rates and changes thereof can be recognized after completion of the exercise.

SUMMARY OF THE INVENTION

An object of the present invention is to enable proper evaluation of the amount of exercise in a pulsimeter.

Another object of the present invention is to enable proper evaluation of the amount of exercise from the start of counting at the time of counting in a pulsimeter.

Still another object of the present invention is to enable proper evaluation of the amount of exercise after counting in a pulsimeter.

In order to attain the aforementioned objects, a pulsimeter according to the present invention comprises a pulse sensor for detecting pulses of a human body, a pulse counter for counting the number of pulses detected in a counting time, and a display for indicating the number of the counted pulses with elapsed time.

In the pulsimeter having the aforementioned structure, the number of pulses detected in counting time is so counted that the count value is displayed with elapsed time. Thus, it is possible to properly evaluate the amount of exercise from the start of counting at the time of counting.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 4 illustrates relations between pulse rates of not more than 99 and consumed calories employed in the embodiment of the present invention;

DESCRIPTION OF THE PREFERRED EMBODIMENTS

Figure 1:
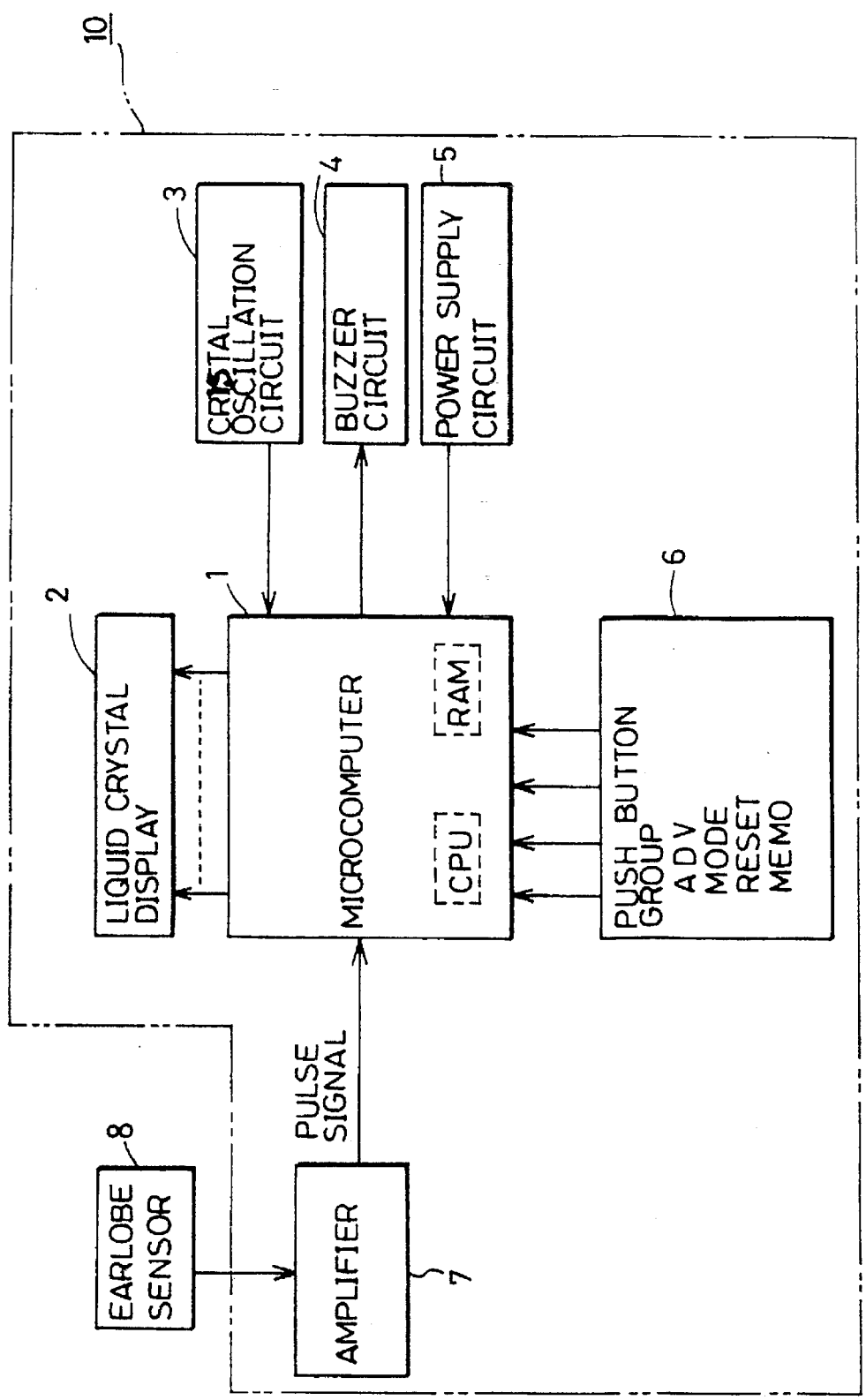
FIG. 1 is a system block diagram showing the structure of a pulsimeter according to an embodiment of the present invention.

FIG. 1 is a system block diagram showing the structure of a pulsimeter 10 according to an embodiment of the present invention.

Referring to FIG. 1, the pulsimeter is formed by an earlobe sensor 8 which is attached to an earlobe of a human body for detecting pulses from changes in light transmittance by the amount of pulsation of blood in the blood capillaries of the earlobe, an amplifier 7 which amplifies and binarizes an analog signal received from the earlobe sensor 8 and outputs the same as a pulse signal, a microcomputer 1 which receives the pulse signal from the amplifier 7, a crystal oscillation circuit 3 which generates clocks for counting a prescribed time, a buzzer circuit 4 for giving warning by an alarm when a prescribed pulse state is reached, a power supply circuit 5 which provides a power supply for operations of the microcomputer i, a push button group 6 including various buttons for commanding the operations of the microcomputer 1, and a liquid crystal display 2 for indicating calculation results of the microcomputer 1 and the like. The earlobe sensor 8 is generally connected with the body 10 of the pulsimeter by a cord.

Figure 2:
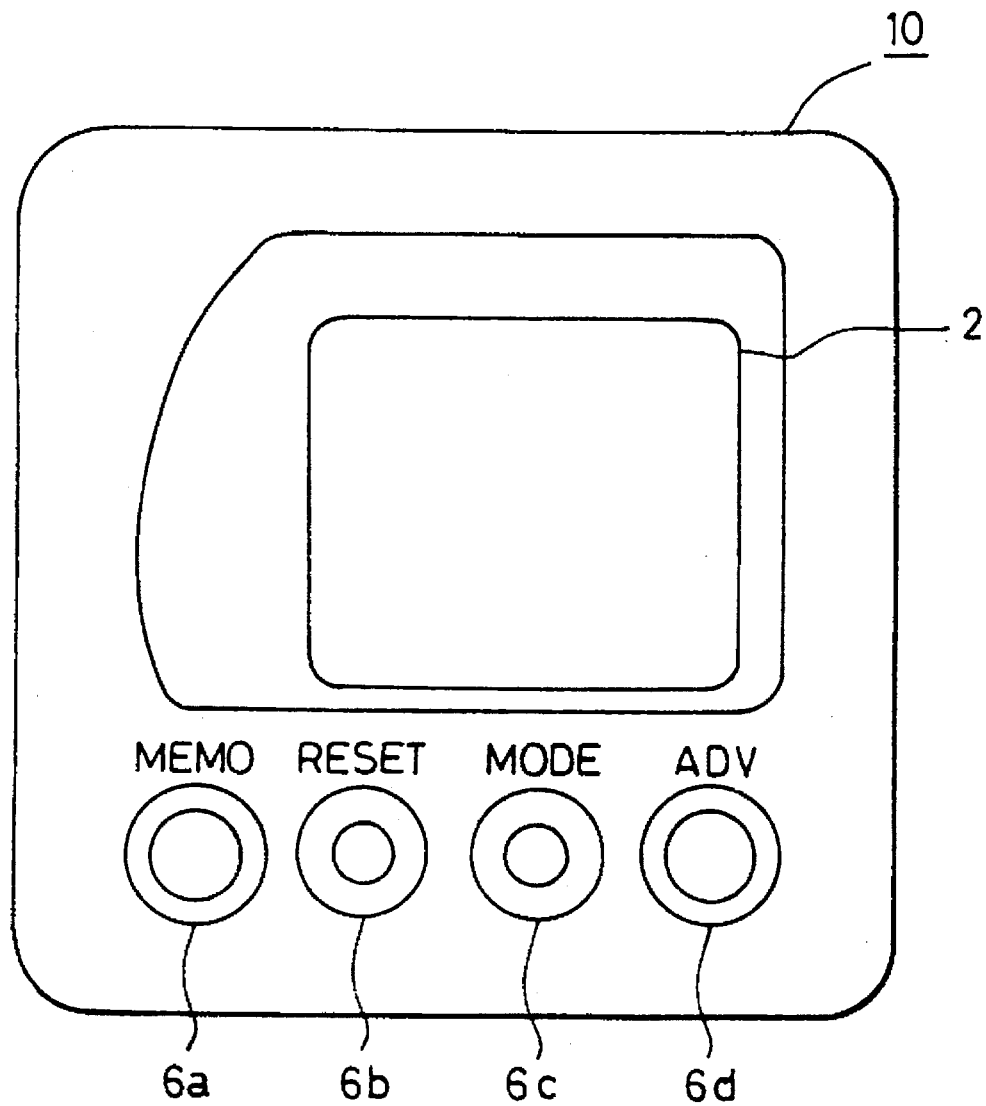
FIG. 2 is a front elevational view showing the appearance of a liquid crystal display shown in FIG. 1.
Figure 3:
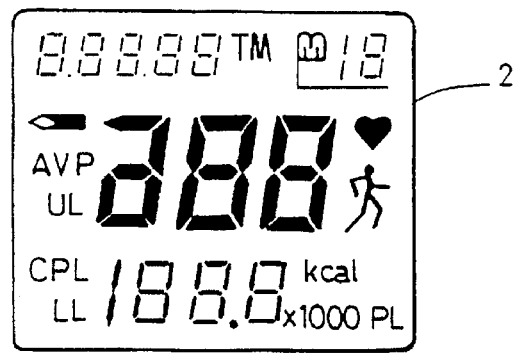
FIG. 3A is an illustration of the liquid crystal display 2 of FIG. 2, showing all indications.
FIG. 3B is an illustration of the liquid crystal display of FIG. 2, showing time, pulse rate and consumed calories indications.
FIG. 3C is an illustration of the liquid crystal display of FIG. 2, showing time, upper limit pulse rate and lower limit pulse rate indications.
FIG. 3D is an illustration of the liquid crystal display of FIG. 2, showing time, average pulse rate and consumed calories indications.
Figure 3:
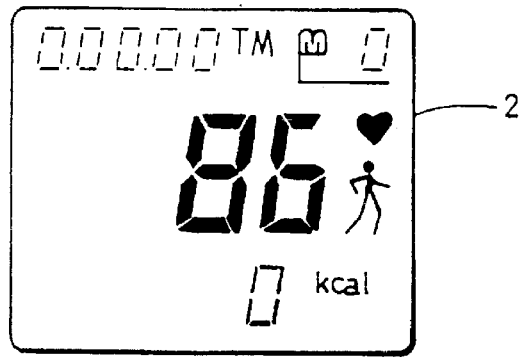
Figure 3:
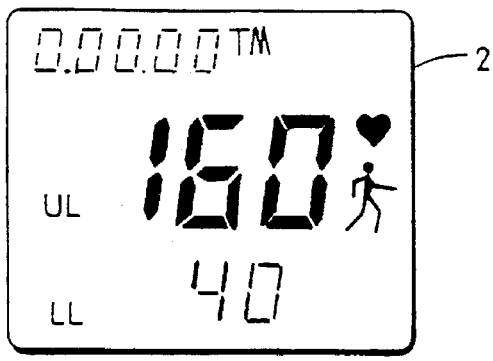
Figure 3:
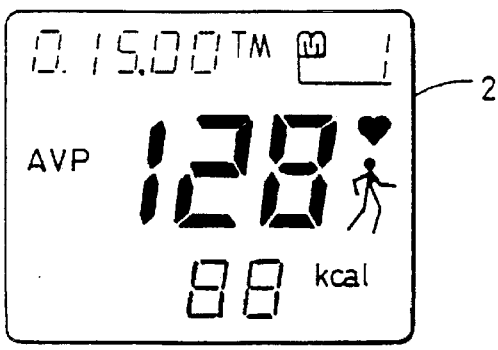

FIG. 2 is a front elevational view showing the appearance of the body 10 of the pulsimeter shown in FIG. 1.

Referring to FIG. 2, the body 10 of the pulsimeter is provided with the liquid crystal display 2 on its central portion and various push buttons including a MEMO button 6a, a RESET button 6b, a MODE button 6c and an ADV button 6d which are arranged under the liquid crystal display 2.

FIG. 3A–3D illustrates various indication states of the liquid display 2. With reference to FIG. 3, basic operations of the pulsimeter 10 according to the embodiment of the present invention will be described.

Upon insertion of a battery, the pulsimeter automatically enters an initial state to light up all indications on the liquid crystal display 2 for 2 seconds, as shown in FIG. 3A. After a lapse of the 2 seconds, the liquid crystal display 2 indicates a setting timer TM (0 in this case), a pulse rate (86) and a consumed calorie (0 kcal in this case), as shown in FIG. 3B. Namely, when the earlobe sensor 8 is set on the human body and power is supplied to the body 10 of the pulsimeter, counting of the pulse rate (number of pulses per minute) is immediately started to indicate the count value while the setting timer TM and the consumed calorie remain in zero indication states.

Then, the ADV button 6d is pushed to start counting, whereby a person indicator is blinked on the liquid crystal display 2. The consumed calorie (kcal) and a number of cumulated pulses (×1000 PL) (hereinafter referred to as "cumulative pulse rate") are counted up in response to the counted pulse rate. It is possible to switch the consumed calorie indication mode shown in FIG. 3B to a cumulative pulse rate indication mode by pushing the MODE button 6c. The liquid crystal display 2 is initially in the consumed calorie indication mode upon power supply.

When the RESET button 6b is pushed for about 2 seconds during the indication of the pulse rate, the indications of the timer TM, the consumed calorie/the cumulative pulse rate and as-set MEMO data are reset. Further, the current indication contents are fixed when the ADV button 6d is pushed, while the power is turned off to cancel the indications on the liquid display 2 when the ADV button 6d is again pushed. If no signal is received from the earlobe sensor 8 or the like for about 1 hour, on the other hand, the pulsimeter is automatically turned off in order to avoid consumption of the power supply. When the ADV button 6d is pushed in a power-off state, the liquid crystal display 2 enters the state shown in FIG. 3B, i.e., a power-on state.

When the MEMO button 6a is pushed for 2 seconds in the state shown in FIG. 3B, the liquid crystal display 2 indicates a set value of the timer TM and upper and lower limit pulse rates UL and LL while blinking "hour" and "minute" display portions in timer setting, as shown in FIG. 3C. These numerical values are increased when the MODE button 6c is pushed in this state, while the same are decreased when the RESET button 6b is pushed in this state. The set values of the timer TM can be changed in this way. When the MEMO button 6a is again pushed, the numerical value portion of the upper limit pulse rate UL is so blinked that the same can be arbitrarily changed in the aforementioned manner. When the MEMO button 6a is further pushed, the numerical value portion of the lower limit pulse rate LL is so blinked that the same can also be arbitrarily changed in the aforementioned manner. When these values are completely set, the ADV button 6d is set so that the liquid crystal display 2 returns to the state shown in FIG. 3B. These set values are stored until the battery for the pulsimeter 10 is exchanged, unless the set contents are again changed.

When a measured pulse rate is in excess of the upper limit pulse rate UL or below the lower limit pulse rate LL, an alarm buzzer is activated. The initial values of the upper and lower limit pulse rates UL and LL are 160 pulses/min. and 40 pulses/min. respectively. The alarm buzzer is made inoperative when the pulse rate is zero, i.e., when the earlobe sensor 8 is unset.

The timer TM can be set at an arbitrary value within a range of 1 minute to 9 hours 59 minutes. When the target time is set at 10 minutes, a buzzer is sounded every 10 minutes to store the current timer value as well as the cumulative pulse rate and the consumed calorie in this period, and a MEMO display value is incremented by 1.

Thus, the buzzer is sounded every target time to store the lapse time and the current consumed calorie/the current cumulative pulse rate. Such data at that time are similarly stored also when the MEMO button 6a is pushed.

In order to access the stored contents, the MODE button 6c is pushed for about 2 seconds so that the liquid crystal display 2 enters a MEMO indication mode to indicate first MEMO data as shown FIG. 3D. The set value of the timer TM, a current average pulse rate AVP and the current consumed calorie are indicated in this example. The MODE button 6c is again pushed in this state, to switch the indication of the current consumed calorie to that of the current cumulative pulse rate.

When the MEMO button 6a is further pushed, a memory number provided on a right upper corner of the screen is incremented by 1 to invoke next storage contents on the screen. In a similar manner, the stored MEMO data are successively indicated on the screen. Finally the ADV button 6d is pushed or the MODE button 6c is pushed for about 2 seconds, so that the screen returns to the state shown in FIG. 3B.

Figures 5, 6:
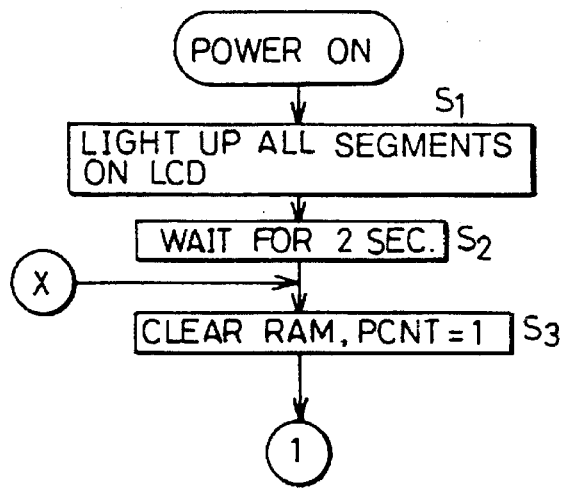
FIG. 5 illustrates relations between pulse rates exceeding 100 and consumed calories employed in the embodiment of the present invention.
FIG. 6 is a part of a flow chart showing the contents of control by a microcomputer 1 appearing in FIG. 1.
Figure 7:
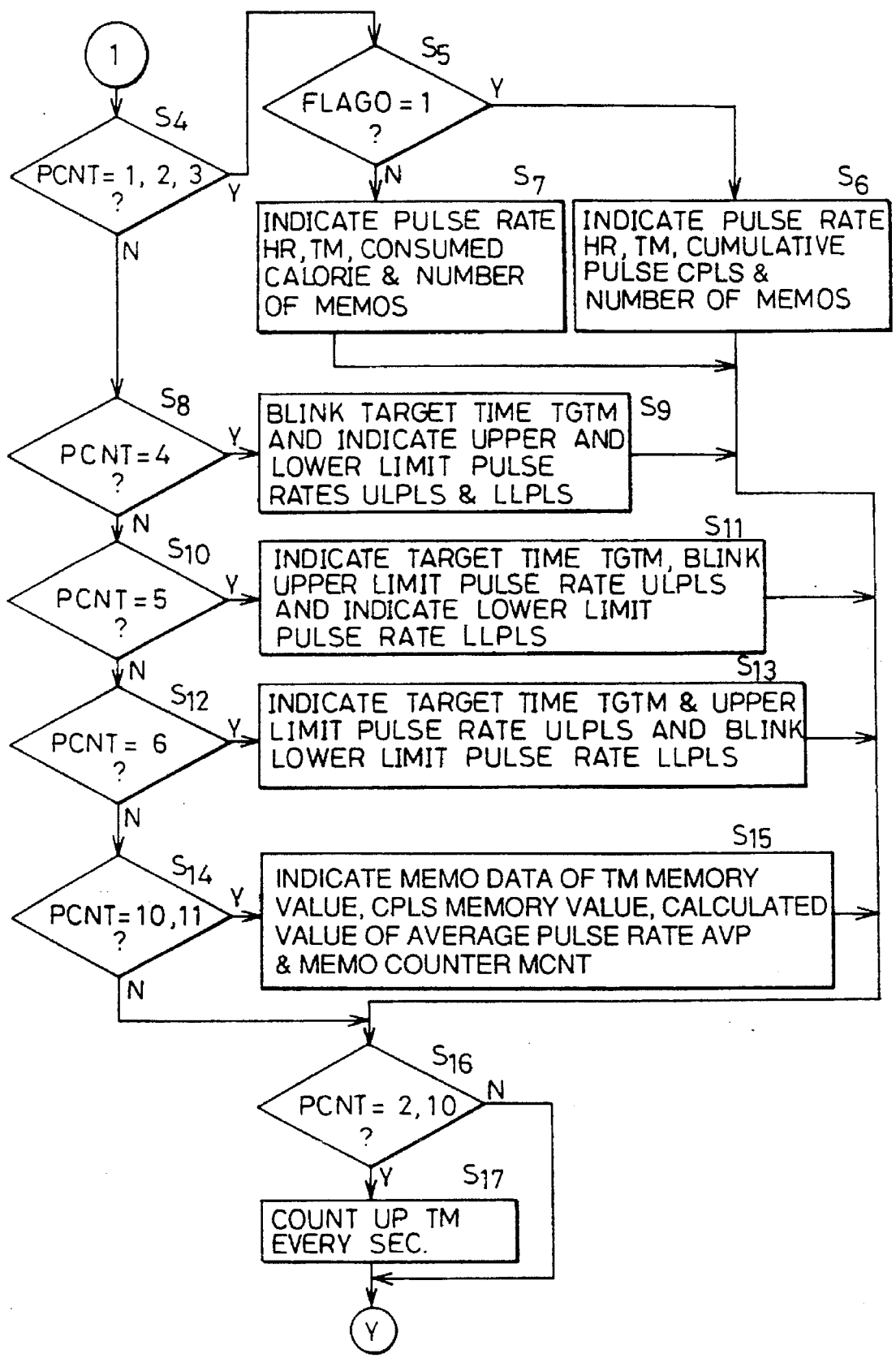
FIG. 7 is another part of the flow chart showing the contents of control by the microcomputer 1 appearing in FIG. 1.
Figure 8:
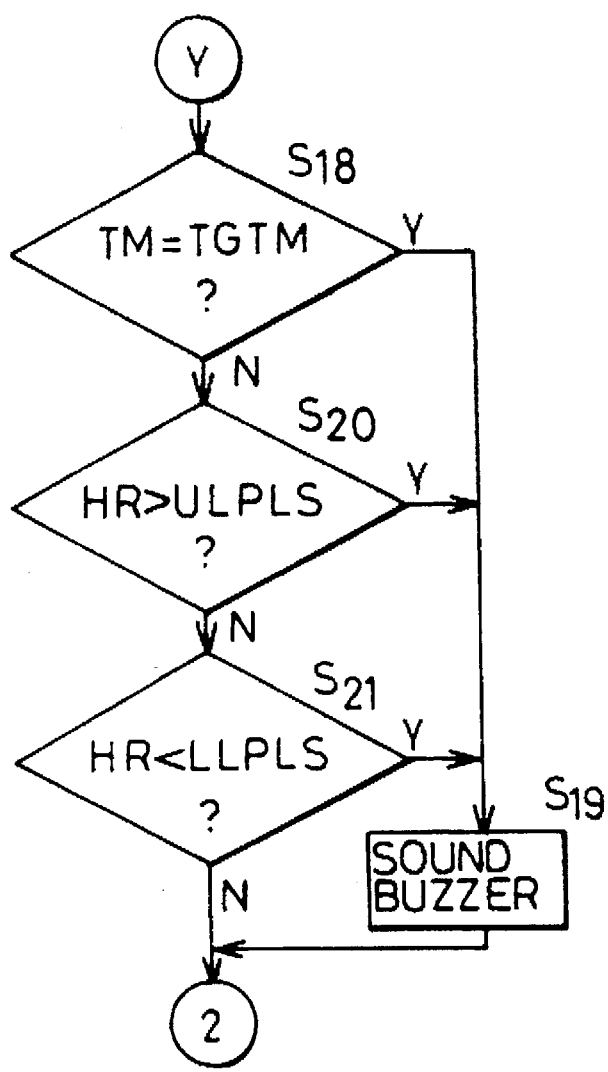
FIG. 8 is still another part of the flow chart showing the contents of control by the microcomputer 1 appearing in FIG. 1.
Figure 9:
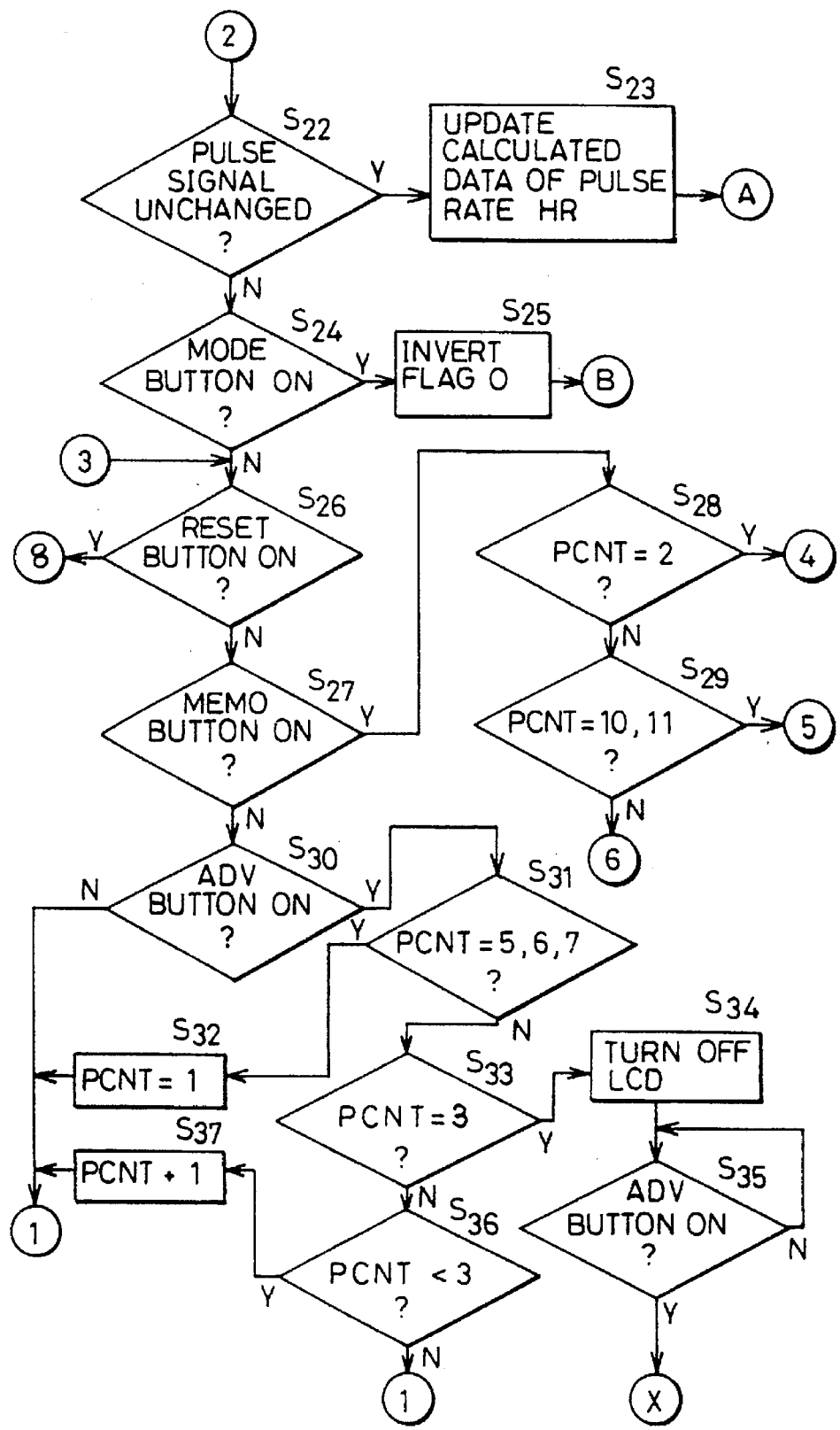
FIG. 9 is a further part of the flow chart showing the contents of control by the microcomputer 1 appearing in FIG. 1.
Figure 10:
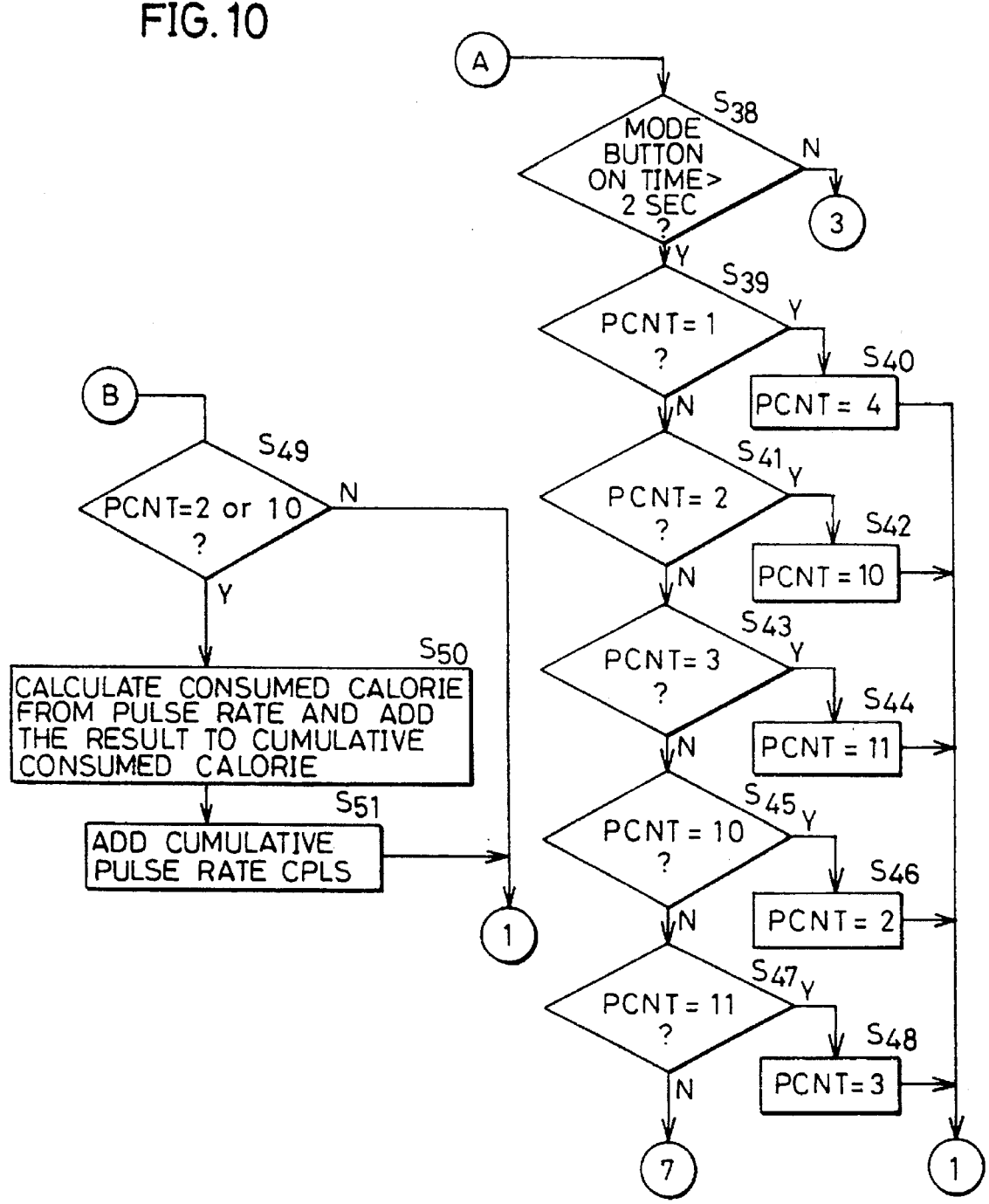
FIG. 10 is a further part of the flow chart showing the contents of control by the microcomputer 1 appearing in FIG. 1.
Figure 11:
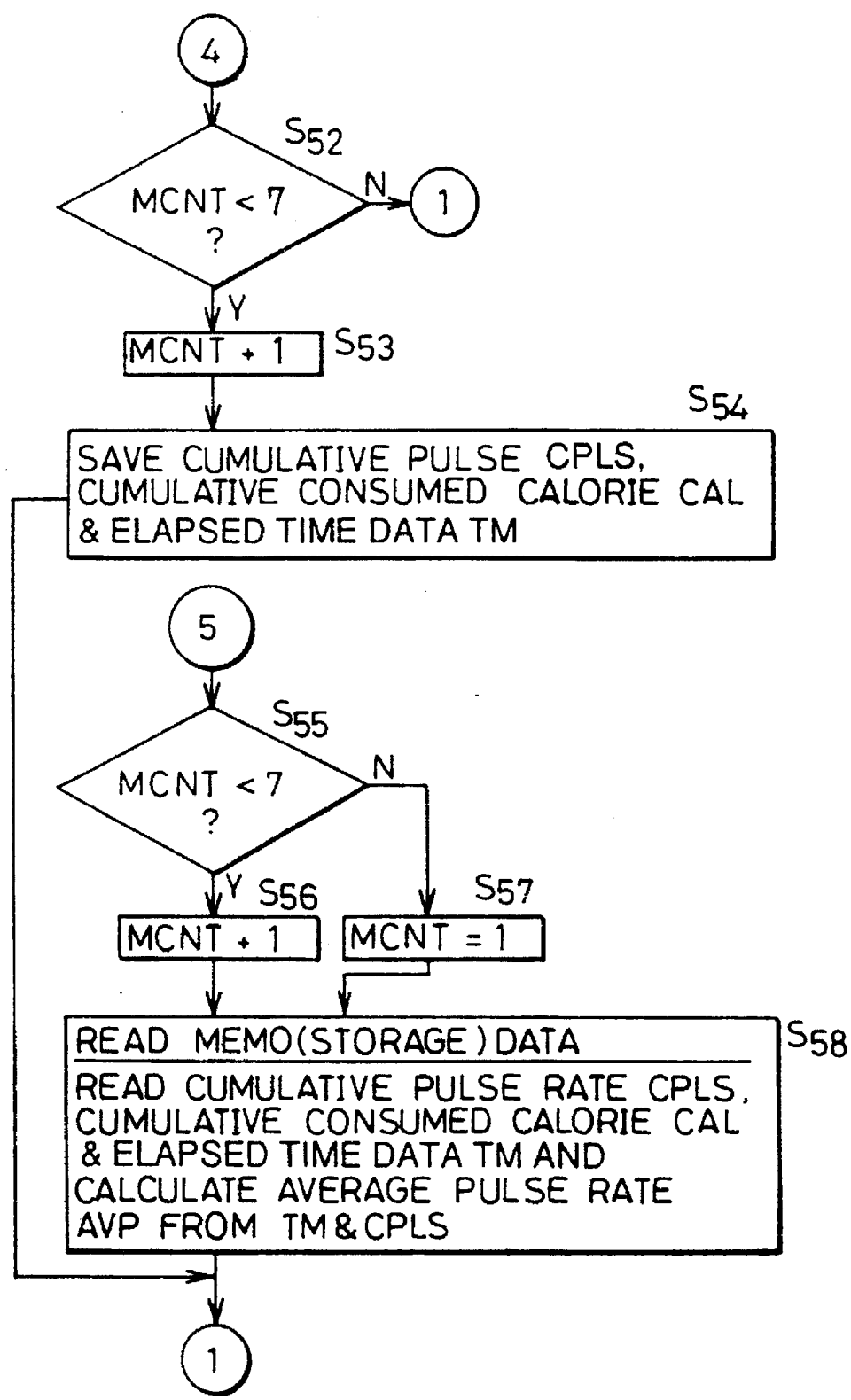
FIG. 11 is a further part of the flow chart showing the contents of control by the microcomputer 1 appearing in FIG. 1.
Figure 12:
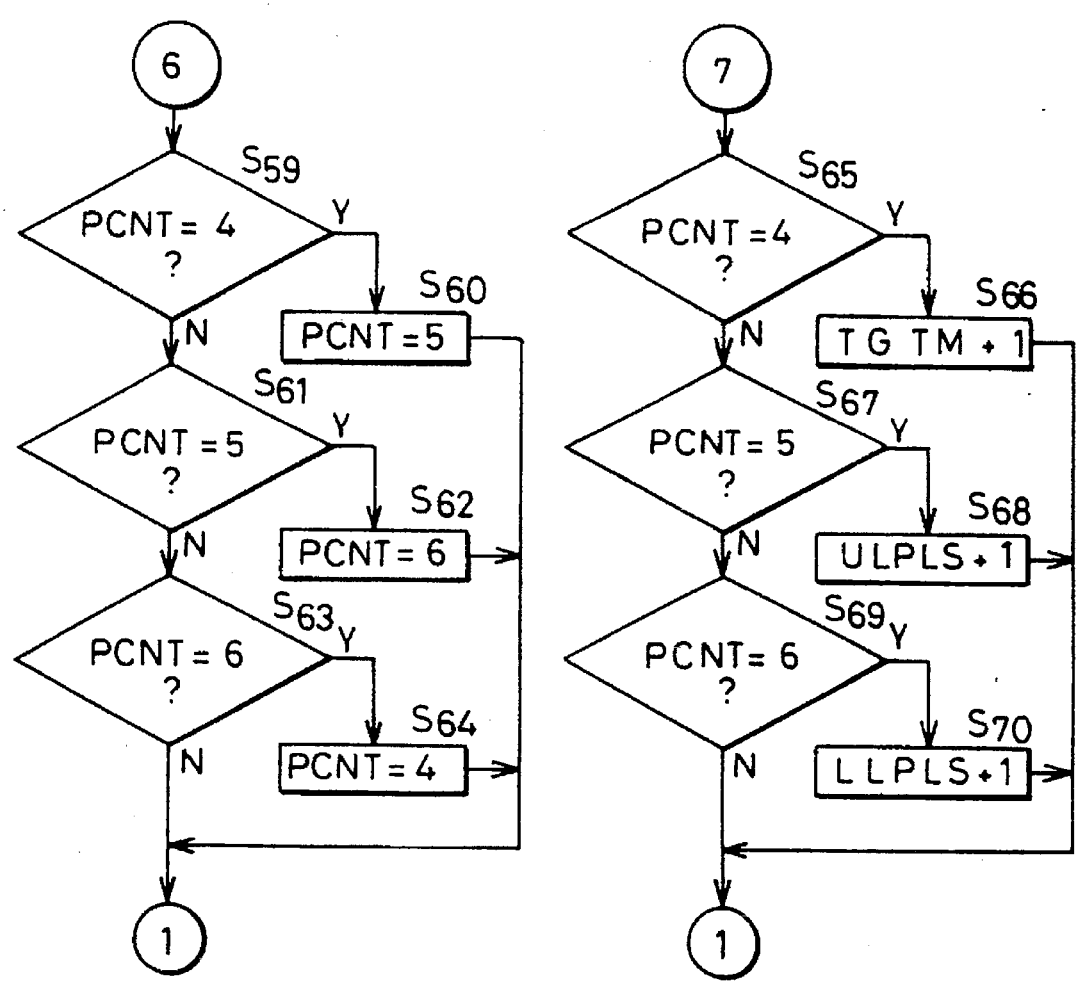
FIG. 12 is a further part of the flow chart showing the contents of control by the microcomputer 1 appearing in FIG. 1.
Figure 13:
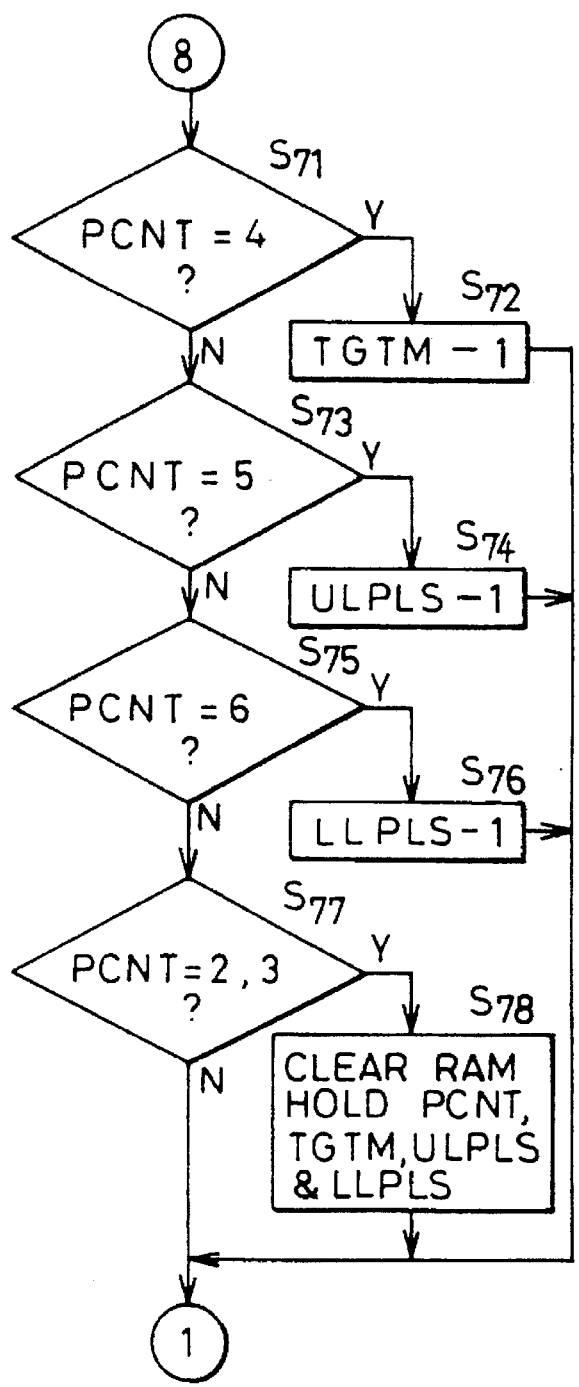
FIG. 13 is a further part of the flow chart showing the contents of control by the microcomputer 1 appearing in FIG. 1.

FIG. 4 illustrates relations between pulse rates up to 99 and consumed calories, and FIG. 5 illustrates relations between pulse rates exceeding 99 and consumed calories.

The consumed calorie is basically calculated every 2 seconds, as shown in FIGS. 4 and 5. Assuming that HR represents a pulse rate exceeding 99, a calorie K consumed every 2 seconds is calculated as follows (refer to "New Edition of Exercise Prescription" by Haruo Ikegami, First Edition, Asakura Shoten, May 10, 1990):

$$K = 0.00250 \times HR - 0.1166$$

FIGS. 6 to 13 illustrate a flow chart showing a process for implementing basic operations of the pulsimeter 10 controlled by the microcomputer 1. The contents of the operations are now briefly described.

First, all segments of the liquid crystal display 2 are lit up and maintained in these states for 2 seconds, and then contents of a RAM provided in the microcomputer 1 are cleared so that a program counter PCNT is initialized at 1 (steps S1, S2 and S3).

At a step S4, a determination is made as to whether or not the program counter PCNT corresponds to any one of 1, 2 and 3. Since the program counter PCNT is initialized at 1 upon power supply, the process advances to a step S5 to determine whether or not a flag O is 1. Since this flag O is initialized at 0, the process advances to a step S7 to indicate the pulse rate, the setting timer TM, the consumed calorie, the number of memos and the like, and then advances to a step S16.

At the step S16, a determination is made as to whether or not the program counter PCNT is 2 or 10, and the process skips a step S17 to advance to a step S18 since the program counter PCNT is set at 1. If the value of the timer TM is set at a target time TGTM or the pulse rate HR is in excess of the upper limit pulse rate ULPLS or below the lower limit pulse rate LLPLS, a buzzer is sounded at a step S19. Otherwise the process advances to a step S22 while keeping the buzzer silent.

At the step S22, a determination is made as to whether or not the pulse signal outputted from the earlobe sensor 8 is changed. Since the pulse signal is regularly changed in general, the process advances to a step S24, and if the ADV button 6d is pushed while the MODE, RESET and MEMO buttons 6c, 6b and 6a are kept untouched, the process advances to a step S31. Since the program counter PCNT is held at 1, the process advances to a step S36 through a step S33, and the program counter PCNT is incremented by 1 at a step S37 in response to the result of determination at the step S36, and the process returns to the step S4.

Since the program counter PCNT is incremented to 2, the process advances to the determination step S16 through the steps S5 to S7. The timer TM is counted up every second at the step S17 since the program counter PCNT is at 2, and the process advances to the step S22 through the steps S18 to S21. When only the ADV button 6d is pushed similarly to the above, the process advances to the step S37 through the step S36, so that the program counter PCNT is incremented to 3. In this state, the process skips the step S17, not to count up the timer. When the ADV button 6d is further pushed, the process advances to the step S33 from the step S30, to cancel the indications on the liquid crystal display 2 at the step S34. When the ADV button 6d is again pushed, the process advances to the step S3 to clear the RAM and initialize the program counter PCNT at 1, thereby repeating processing similar to the above. Contents of processing with the remaining buttons are shown in the flow chart, and hence redundant description is omitted.

According to the present invention, as hereinabove described, the number of counted pulses is indicated with elapsed time, whereby it is possible to easily obtain estimation of the amount of exercise up to the pulse detecting time (refer to "Evaluation of Amount of Body Activity for One Day by Scoring the Number of Pulse Rate" by Takashi Kitaura and Tetsuo Numa, 40th Proceedings of the Physical Society of Japan, Oct. 12 to 14, 1989).

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pulsimeter comprising:
   pulse detecting means for detecting pulses of a human body;
   pulse cumulating means for cumulating a number of said detected pulses (CPLS) to produce a cumulated number of said detected pulses, within a predetermined time from said start of counting;
   display means for indicating said (cumulating) cumulated number of said detected within said predetermined time;
   pulse rate calculating means for calculating a pulse rate (AVP) based on said cumulated number of said detected pulses;
   consumed calorie calculating means for calculating the consumed calories per constant time on the basis of said calculated pulse rate;
   consumed calorie cumulating means for cumulating said calculated consumed calories during said predetermined time from the start of counting, at the time of counting;
   said display means also indicating said cumulated consumed calories warning means providing a warning, characterized in that
   said warning means provides a warning for every lapse of said predetermined time from the start of counting, thus providing a continuous record of pulse rate and wherein time setting means are provided for setting said predetermined time.

2. A pulsimeter in accordance with claim 1, further comprising:
   memory means for storing said number of said detected pulses and said cumulated consumed calories every said predetermined time.

3. A pulsimeter in accordance with claim 2, further comprising:
   storage designating means for designating an arbitrary one of a plurality of continuous storages, each storage containing said cumulated number of said detected pulses (CPLS) and said cumulated consumed calories (CAL) for a respective of each of said predetermined time (TGTM),
   wherein said display means indicates said cumulated number of said detected pulse (CPLS) or said cumulated consumed calories (CAL) being stored in said memory means with respect to said designated storage in response to a designation output from said storage designating means.

4. A pulsimeter according to claim 3 comprising average pulse rate calculating means for calculating an average pulse rate in said predetermined time based on said cumulated number of said detected pulses.

5. A pulsimeter according to claim 2 comprising average pulse rate calculating means for calculating an average pulse rate in said predetermined time based on said cumulated number of said detected pulses.

6. A pulsimeter according to claim 1, further comprising,
   average pulse rate calculating means for calculating an average pulse rate in said predetermined time based on said cumulated number of said detected pulses.

7. A pulsimeter in accordance with claim 6, further comprising:
   storage designating means for designating an arbitrary one of a plurality of continuous storage, each storage containing said average pulse rate for a respective of each of said predetermined times,
   wherein said display means indicates an average pulse rate with respect to said designated storage in response to a designation output from said storage designating means.

8. A pulsimeter in accordance with claim 7 comprising:
   instruction means for instructing a starting of a counting of the pulses, said pulse cumulating means cumulating the number of said detected pulses in response to an instruction output from said instruction means; and
   said display means indicating a current said accumulated number of said detected pulses (CPLS).

9. A pulsimeter in accordance with claim 8 further comprising:
   determining means for determining a pulse rate based on said number of said detected pulses,
   calculating means for calculating a current consumed calorie on the basis of said determined pulse rate in response to an instruction output from said instruction means, switching instruction means for instructing switching of indications on said display means, and control means for controlling said display means to indicate said calculated consumed calorie in place of said cumulated number of said detected pulses (CPLS) in response to an instruction output from said switching instruction means.

10. A pulsimeter in accordance with claim 6 further comprising:

determining means for determining a pulse rate based on said number of said detected pulses, calculating means for calculating a current consumed calorie on the basis of said determined pulse rate in response to an instruction output from said instruction means, switching instruction means for instructing switching of indications on said display means, and control means for controlling said display means to indicate said calculated consumed calorie in place of said cumulated number of said detected pulses in response to an instruction output from said switching instruction means.

11. A pulsimeter in accordance with claim 1 comprising:

instruction means for instructing a starting of a counting of the pulses, said pulse cumulating means cumulating a number of said detected pulses in response to an instruction output from said instruction means; and said display means indicating the accumulated number of said detected pulses.

12. A pulsimeter in accordance with claim 11 further comprising:

determining means for determining a pulse rate on the basis of said number of said detected pulses, calculating means for calculating a current consumed calorie based on said determined pulse rate in response to an instruction output from said instruction means, switching instruction means for instructing switching of indications on said display means, and control means for controlling said display means to indicate said calculated consumed calorie in place of said cumulated number of said detected pulses in response to an instruction output from said switching instruction means.

* * * * *